US011992689B2

(12) United States Patent
Possover

(10) Patent No.: US 11,992,689 B2
(45) Date of Patent: May 28, 2024

(54) SYSTEM FOR NEUROMODULATION

(71) Applicant: Marc Possover, Hagendorn (CH)

(72) Inventor: Marc Possover, Hagendorn (CH)

(*) Notice: Subject to any disclaimer, the term of this patent is extended or adjusted under 35 U.S.C. 154(b) by 298 days.

(21) Appl. No.: 16/956,570

(22) PCT Filed: Dec. 22, 2017

(86) PCT No.: PCT/EP2017/084436
§ 371 (c)(1),
(2) Date: Jun. 20, 2020

(87) PCT Pub. No.: WO2019/120568
PCT Pub. Date: Jun. 27, 2019

(65) Prior Publication Data
US 2021/0370074 A1  Dec. 2, 2021

(51) Int. Cl.
*A61N 1/372* (2006.01)
*A61N 1/05* (2006.01)
(Continued)

(52) U.S. Cl.
CPC ....... *A61N 1/37223* (2013.01); *A61N 1/0558* (2013.01); *A61N 1/36128* (2013.01); *A61N 1/378* (2013.01)

(58) Field of Classification Search
CPC .............. A61N 1/37223; A61N 1/0558; A61N 1/36128; A61N 1/378; A61N 1/36003;
(Continued)

(56) References Cited

U.S. PATENT DOCUMENTS 4,573,481 A * 3/1986 Bullara ................ A61N 1/0556
607/118
6,269,266 B1 * 7/2001 Leysieffer ............ H04R 25/554
607/2
(Continued)

FOREIGN PATENT DOCUMENTS

EP     2767306 A2   8/2014
WO  2008021524 A2   2/2008
(Continued)

OTHER PUBLICATIONS

International search report for patent application No. PCT/EP2017/084436 dated Jul. 17, 2018.

*Primary Examiner* — Mallika D Fairchild
(74) *Attorney, Agent, or Firm* — Bachman & LaPointe, P.C.

(57) ABSTRACT

The invention relates to a system, which can be implanted in a human body, for neuromodulation of nerves, having an electronic signal generating or in an implantable signal generating housing (10), a voltage supply connected to the signal generating or, at least one elongated multi-channel wire electrode (12), which is connected to the signal generating housing and which is designed for implantation in the human body on a nerve (DNP), which multi-channel wire electrode forms a plurality of shell segment electrodes (16a-16d) on a nerve contact region (14) and has, on the ends thereof, a fixing (18) for anchoring the wire electrode means to an implantation location, wherein the signal generator housing has a flat fixing unit (20), which is flange-like and/or sits and/or protrudes in the manner of a piece of tissue, which enables the surgical fixation of the signal generating housing to a tissue, muscle or bone region (PB) in the body, in particular to a region of the pubic bone, to a muscle portion and/or to a fascia.

18 Claims, 2 Drawing Sheets

(51) Int. Cl.
*A61N 1/36* (2006.01)
*A61N 1/378* (2006.01)

(58) Field of Classification Search
CPC ............ A61N 1/36007; A61N 1/36062; A61N 1/37518
See application file for complete search history.

(56) References Cited

U.S. PATENT DOCUMENTS

| | | |
|---|---|---|
| 2003/0028179 A1 | 2/2003 | Piskun |
| 2003/0114905 A1* | 6/2003 | Kuzma ................ A61N 1/0551 607/116 |
| 2008/0132982 A1* | 6/2008 | Gerber ................ A61N 1/0558 607/116 |
| 2010/0312320 A1* | 12/2010 | Faltys .................. A61N 1/0556 607/118 |
| 2010/0318098 A1* | 12/2010 | Lund .................... A61N 1/0524 606/129 |
| 2014/0058240 A1* | 2/2014 | Mothilal .............. A61B 5/0215 29/601 |
| 2014/0228905 A1 | 8/2014 | Bolea |
| 2015/0088155 A1* | 3/2015 | Stahmann ........... A61N 1/0587 606/129 |

FOREIGN PATENT DOCUMENTS

| | | | |
|---|---|---|---|
| WO | 2017044904 A1 | 3/2017 | |
| WO | WO-2017213978 A1 * | 12/2017 | ........... A61N 1/0541 |

* cited by examiner (b)

(b)

(c)

(d)

SYSTEM FOR NEUROMODULATION

BACKGROUND OF THE INVENTION

The invention relates to a system for neuromodulation.

Such a system is known from EP 2 389 975 B1 of the applicant, for example, and describes, in particular, wire electrode means which are advantageously adapted to the specific implantation conditions in a pelvic floor area of the human body and which allow in a generic manner for the stimulation and neuromodulation of the nerves, in particular nerve roots, which are contacted in a corresponding manner.

In the context of the present application of implanting systems for neuromodulation of nerves, EP 2 767 306 A1 of the applicant discloses an implantation tool which facilitates the implantation process and additional preferred embodiments and realizations, in particular of the generic multi-channel wire electrode means, i.e. in such a manner that said wire electrode means have fixing or armature means, in particular at the end of the electrode on the side of the operation (i.e. which are assigned to a corresponding nerve at the implantation location), which avoid or prevent an unintentional pulling back or other movement processes which detach an operation state at the implantation location—in the case of EP 2 767 306 cited with respect to the state of the art, said fixing or armature means are armature structures which are similar to barbs and which anchor the wire electrode means which are guided to the implantation location by interacting with a surrounding muscle or connective tissue.

WO 2017/044904 A1 discloses a method for treating a patient, comprising the provision of a medical apparatus comprising an external system and an implantable system, the method also comprising the implanting of the implantable system and the delivery of at least one of power or data to the implantable system with the external system. The external system comprises: at least one external antenna configured to transmit a first transmission signal to the implantable system; an external transmitter configured to drive the at least one external antenna; an external power supply and an external controller. The implantable system comprises: at least one implantable antenna configured to receive the first transmission signal from the first external device; an implantable receiver; at least one implantable functional element configured to interface with the patient; an implantable controller; an implantable energy storage assembly; and an implantable housing surrounding at least the implantable controller and the implantable receiver. Medical devices are also available.

US 2010/312320 A1 describes an extravascular nerve cuff configured to receive a leadless, integrated, implantable micro stimulator. The nerve cuff can comprise a cuff body having a pocket or pouch configured to removably hold the implantable device. The nerve cuff can be fixed around the nerve in such a manner that the electrodes of the device are in a stable position relative to the nerve. Additionally, the nerve cuff drives the majority of the current from the stimulation device into the nerve and protects the surrounding tissue against undesired stimulation.

Furthermore, a method for treating a patient is known from US 2014/228905 A1 which comprises the following method steps: sensing a biological parameter indicative of respiration; analyzing the biological parameter to identify a respiratory cycle; identifying an inspiratory phase of the respiratory cycle; and delivering stimulation to a hypoglossal nerve of the patient, wherein stimulation is delivered if a duration of the inspiratory phase of the respiratory cycle is greater than a predetermined portion of a duration of the entire respiratory cycle.

Whereas the disclosures which are cited in an exemplary manner with respect to the state of the art and which document, in particular, significant progresses made by the applicant and devised on the basis of the implantation practice are to be understood as generic technologies and are suitable for a plurality of stimulation functions and indication on the basis of typical signal transmitters of pacemakers as signal generating means, connected to multi-channel wire electrodes—in this regard, the applicant is responsible for advantageous medicinal benefits achieved, in particular, through the so-called LION surgical approach—, further optimization or improvement is needed with respect to the increasing specialization of implantation requirements and a desired configurability of generic systems used for neuromodulation of nerves.

It is usual and known to connect single-channel or multi-channel signal generators of pacemakers as generic signal generating means in a suitable manner to the aforementioned multi-channel wire electrode means (and realizing a plurality of shell segment electrodes on the side of the operation), to provide them in the abdominal area to allow for a simple explantation for the purpose of maintaining or exchanging the signal generator, for example, while the wire electrodes, enabled by surgical approaches according to the LION method, are guided to and kept at the area of application, such as the inner pelvic floor. However, said generic technology does not take into account the fact that, depending on a respective indication and a corresponding application (use) of the implanted system or the system to be implanted, simpler or more complex signal patterns are to be generated (in a corresponding manner, the requirements of the signal generator electronics can be different) and the fact that different, also several stimulation or neuromodulation purposes may be required in the body; in such a case, a plurality of generic systems each having an assigned, specified surgical approach and indication would be implanted.

Furthermore, the variance of the possible purposes and modulation or stimulation functions in the human body, in particular in the pelvic floor area, has an impact on the different electrical energy supply expense related thereto. While either batteries (to be replaced) or rechargeable power supply units (from the extracorporeal) are provided in known signal generator housings, in particular their electrical capacity or a need to (re)charge or to exchange (in this case related to an increase of the burden by a new surgical opening of the body) is usually not specifically adapted or optimized, unnecessary surgical processes thus being caused in practice, in extreme cases even an electrical energy undersupply of the already implanted patient, said fact involving disadvantages and risks, in particular with respect to critical modulation or stimulation processes for maintaining important bodily functions.

Furthermore, a common problem is that an implanted signal generator housing—typically implanted in the aforementioned manner in the abdominal area of the human body—has to be localized in a laborious manner, in particular in the case of a long-term use and a necessary external access (for example for the purpose of exchanging), said localization being linked to problems of determining an exact orientation or position of the signal generator housing in the body from the extracorporeal, said fact having a corresponding negative impact on a (desired) short time of access and explantation.

SUMMARY OF THE INVENTION

Against the background of said problems arising from the practical implantation context, the object of the present invention is to create a system for neuromodulation of nerves which can be implanted in a human body and which is optimized with respect to the electronic signal generating means and the wire electrode means connected thereto and to be implanted together with said signal generating means as a system and with respect to specific indications or indications to be specified. In this regard, in particular a later access to or a localization of the signal generator housing of the signal generating means is to be simplified and the condition is to be created for keeping the wire electrode means which sit at the signal generator housing or which transmit the modulation or stimulation signals to the nerve at the location in a reliable manner and to ensure their operational safety. Additionally, the implantation of a generic system is to be improved and simplified, in particular with respect to an exact positioning of the wire electrode means including the nerve contact area at the respective nerve.

Said object is attained by the implantable system for neuromodulation as disclosed herein; advantageous embodiments of the invention are also disclosed herein and in the dependent claims.

In an advantageous manner according to the invention, the signal generator housing has a flat fixing section which is flange like and/or realized in the manner of a piece of tissue and which sits at the housing and/or protrudes and by means of which a surgeon who implants the system according to the invention in the body can fix said generator housing by surgical fixation to a bone area in the body.

An area of the pubic bone is particularly preferably selected as such a bone area, because, in order to attain the object and in an advantageous manner according to the invention, not only a secure implantation position which is easy to access and which is favorable to the electrode wire which is coupled to the signal generator housing (for indications relating to the pelvic floor), but it also allows, in particular, for the implantation and fixation in the area of the pubic bone, realized in an advantageous manner according to the invention by the flat fixing section, from the extracorporeal and for transmitting different signals through the skin or muscle layer which covers the pubic bone, wherein said signals can supply electric charge energy from the extracorporeal, for example, to the housing which is safely fixed in the body and it is also possible (and provided according to advantageous embodiments according to the invention), to realize a desired operating state of the system by means of wireless control, parameterizing and/or operating mode means which are configured in a suitable manner.

In this respect, the present invention is to be understood so as to be synergistic in multiple ways, because the invention provides for a physical-mechanical fixing state of the signal generator housing in the body which facilitates future (surgical) accesses (at the same time, the invention allows for a defined orientation and thus improves the guide and contact safety of the corresponding electrode wire (wire electrode means)) and the condition for the aforementioned control or parameterization of different operating or setting modes to be determined from the extracorporeal is given by the defined implantation position.

In an advantageous manner according to the invention and in an embodiment of the invention, the fixing section is realized so as to be elastically deformable and has predefined openings or openings which are entirely or partially shaped into the fixing section (more preferably, said openings can be provided in the form of a regular shaped pattern), alternatively in the form of a nonwoven fabric polymer material and/or tissue, in order to be able to realize the fixation to the bone area by means of suture material, screws, nails, clamps or other methods in a short time of surgery, at a high quality of fixation and a minimum of burdens for patient by the aforementioned operation by a surgeon.

In practice, it has proved to be particularly advantageous to realize the fixing section according to the invention axially on both sides (both ends) of narrow sides of a signal generator housing, wherein said signal generator housing can additionally and advantageously be realized in an elongated manner within the scope of said embodiment. Said realization allows for the guiding (orientation) of the housing along a narrow pubic bone section, the flange-like sections on the end portions allowing for a particularly simple and secure mechanical connection to the bone.

The fixation of the signal generator housing to the bone area enabled and provided by the present invention also defines the end of the wire electrode means on the side of the feeding or signal generator. For further optimization of the guiding and safety of said wire electrode means, an additional advantageous embodiment of the invention provides to secure the wire electrode means by fixing means (more preferably at the end on the side of the nerve and of the operation) which provide a grommet to be fixed by means of suture material in the implanted state. Said grommet provided at the free end of the electrode wire enables, in particular, those surgeons to ensure a secure anchoring of the electrode means (in particular secured against an unintentional pulling back of the wire) who can create fast and secure suture material knots from their usual surgical practice. In this regard, the grommet according to the embodiment has a significant fixation advantage compared to known barbs for anchoring the electrodes.

Furthermore, the latter advantageous embodiment is particularly advantageous if, according to an additional advantageous realization of the invention, the signal generator housing provides a detachable fixing (for example by a suitable plug-socket combination) of the electrode wire. In such a case, the signal generator housing can be exchanged without explanting the electrode wire (which already sits at the implantation location and may be already ingrown), the signal generator housing being not only exchanged for the purpose of exchanging a voltage supply, but also in the case of technical updates, developments or similar changes when an implanted system is operated and carried over a long period of time (typically long-term and up to several years). Additionally, the detachability of the electrode from the signal generator housing provided in an embodiment according to the invention allows to provide a plurality of wire electrode means in an advantageous manner at a (single) signal generator housing which can have multiple channels and which can be realized for the simultaneous signal generation for a plurality of wire electrodes which can be guided (and fixed in a corresponding manner by means of the grommets in a potential embodiment) to potentially different implantation locations (having different indications). The idea of the plug or socket connection in an embodiment according to the invention does not only allow to provide the detachability with respect to the wire electrodes, but also to realize an electrical voltage or energy supply so as to be exchangeable and detachable in a flexible manner (if applicable, in a redundant manner or by an additional housing (voltage supply housing) which is provided for the purpose of implantation and in addition to the signal generator housing).

Concerning said embodiment, almost any realizations are available within the scope of the invention—it is possible, for example, to realize the energy supply of the signal generating means which is enabled by means of said (additional) voltage supply means so as to be chargeable from the extracorporeal (for example in an inductive manner through the abdominal wall by implanting the voltage supply housing near the surface); additionally or alternatively, it is conceivable to convert body's energy, i.e. the thermal energy, by means of thermally efficient voltage generating means into electrical energy and to allow for an energy supply which is potentially independent of batteries or an external energy supply. In particular the progress in the fields of microelectronics, the energy-saving integrated circuitry and a more precise control of the signal (associated with lower modulation or stimulation levels) offer a usability of such autonomous energy systems.

Within the scope of an additional preferred embodiment of the present invention, it is possible to realize the system according to the invention so as to be preconfigured to predefined indications. To this end, the signal generating means according to the invention provided in the signal generator housing are configured for realizing a signal generating pattern (signal pattern) for the control of the electrodes which corresponds to said indication, no specific additional programming thus being required (if applicable and as a possible embodiment, switching allows to select from a limited number of preconfigured signal generating patterns). The wire electrode (wire electrode means) (more preferably connected in a fixed and undetachable manner to the signal generator housing) is adapted in a corresponding manner to the indication, for example with respect to an electrode length, and/or a number and/or a disposition of shell segment electrodes, a system adapted to the desired indication thus being implantable by a minimum of work needed for the setting and configuration. Additionally, said system has the advantage that the manufacturability is simplified and the expense for the hardware is minimized, advantages with respect to the efficiency and the costs thus being realizable in this regard. If there is a need to treat at several nerves inside the body or to implant more than one electrode for different stimulation purposes, a plurality of such preconfigured and simplified systems (each preconfigured) could be implanted. Furthermore, such systems which are specifically adapted or preconfigured with respect to specific indications have the advantage of a low electrical energy absorption and it is expected that a (battery) electricity supply source in the signal generator housing does not have to be exchanged (or charged) over the entire system life and has the potential for improving the costs and the efficiency.

Within the scope of the invention and according to an embodiment, the aforementioned flexible options for connecting implanted signal generator and/or voltage supply housings also provide the possibility to couple two signal generator housings (each having signal generating means provided therein) in a suitable manner by wire means when said two signal generator housings are jointly implanted in a human body. Such a coupling (by wire means) can be realized as a coupling which is based on supply voltage (a supply voltage source of a first housing thus being able to supply the second housing); additionally or alternatively, a signal and/or data communication could be realized, for example for the purpose of synchronizing the (at least two) signal generating means in a suitable manner, for example with the aim of preventing a common operation which is therapeutically undesirable.

As discussed above, the fixation according the invention of the signal generator housing to the bone area of the body allows for the extracorporeal control by the control, parametrizing or operating mode means which are provided according to the embodiment (and which are, in particular, realized for the mobile or portable operation, more preferably the manual handling): By means of conventional technologies, such as Bluetooth or other communication technologies based on high frequency (and more preferably digital), a simple and reliable communication with the implanted signal generator housing can be established, suitable operating modes and/or parameterizations of the implanted system thus being settable, definable and controllable by the attending physician or, additionally or alternatively, by the implanted patient. In addition to a (simple) switching on and off of signal generating electronics which are, for example, implanted for the purpose of sexual stimulation and which are connected to an electrode which is oriented in a corresponding manner, almost any constellations are conceivable in order to affect the behavior of the implanted system. According to an embodiment, such a communication can also be realized in a bidirectional manner, for example for the purpose of receiving direct operating mode, status or warning signals outside the body, a significantly improved quality control of the operation of the implanted system, including specific security mechanisms, thus being conceivable. In this respect, a particularly preferred embodiment of the invention provides that the control, parameterizing or operating mode means according to the invention have means for the acoustic and/or optical representation of different configuration, voltage supply or other operating modes of the signal supply means which can be received on the extracorporeal (typically in a bidirectional communication operation) and which can be processed for the monitoring or diagnosis. Additionally, it is useful for the data and manipulation or access security to realize said operation in a user-identifying or device-identifying manner.

The electrode wire guide means provided according to the invention are realized in the form of an elongated and curved sleeve which has a operation section, preferably on one end, for the manual guiding. According to the invention, said sleeve also has a mandrel which is provided in the sleeve on the insertion end opposite to the handling area (operation section) and which has a point for penetrating the human body tissue, allows for the insertion into the human body, for example from a rectal-extracorporeal direction, to an intended implantation position, preferably controlled in a laparoscopic-endoscopic manner. After removing the mandrel (which can be detached from the actual sleeve), preferably by pulling out the mandrel along the insertion direction (and a removal through the working channel of the endoscope, for example), the wire electrode (wire electrode means) can be inserted through the sleeve (electrode wire guide means) (by gripping the wire electrode on the (open) end portion of the sleeve and inserting the wire electrode by surgery) from the direction of the implantation position (i.e. when the signal generator housing is already inserted and the wire electrode sits thereon—preferably in an undetachable manner). After pulling out the electrode wire guide means (in this case against the insertion direction), the electrode already sits on the correct position at the intended nerve. Within the scope of preferred indications for the use of the invention, the system which has the electrode wire guide means can be used, in particular, in order to take wire electrode means to nerves which are relevant for the genital or sexual stimulation (such as the nervus cavernosi (erectile tissue nerve)) or to a section of the spinal nerve which is assigned to the penis or the clitoris.

As a result, the present system according to the invention allows for new and surprising possibilities with respect to the implantation itself and with respect to the operation of the improved system according to the invention and it is to be expected that the present invention significantly increases the safety and quality of the implantation processes which are enabled by said system. Furthermore, it is to be expected that the operational safety, the ease of use and the safety of the system can be significantly improved when the system is operated (even for several years) in the implanted state.

BRIEF DESCRIPTION OF THE DRAWINGS

Further advantages, features and details of the invention can be derived from the following description of preferred exemplary embodiments and from the drawings.

In the following.

DETAILED DESCRIPTION

Figure 1:
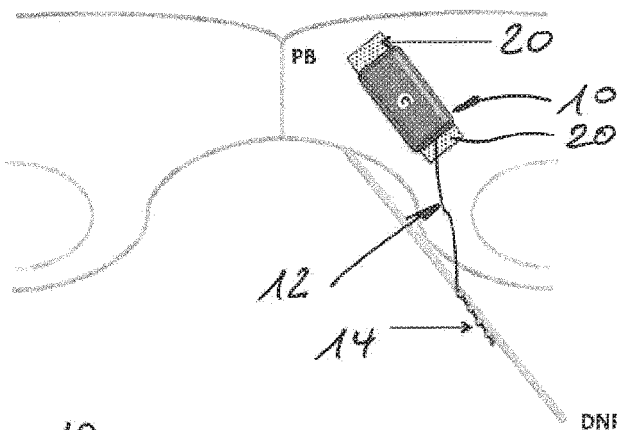
FIG. 1 is a schematic view of the system according to the invention for neuromodulation which has a signal generator housing, in an exemplary manner fixed to the pubic bone of a human body, and a wire electrode which is connected to the signal generator housing (or the signal generating means accommodated therein) and which is guided to a section of the dorsal nerve (of the corresponding sex organ, such as the penis or the clitoris) and which wraps said nerve section by means of its nerve contact area.
Figure 2:
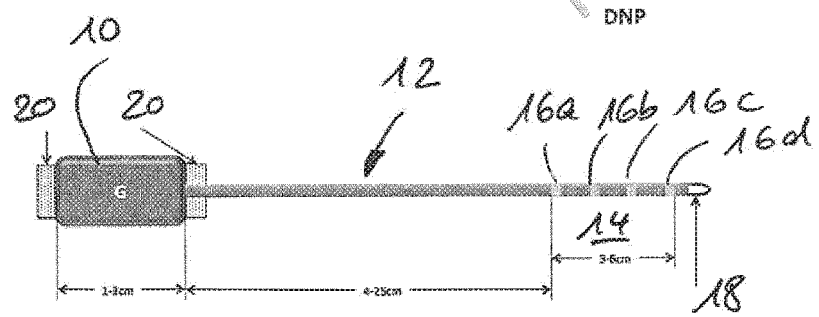
FIG. 2 shows, in section figures (a) and (b), views of the combination of the signal generator housing and wire electrode means which sit thereon and which have exemplary dimensions, in particular for the indication or use in the exemplary embodiment of FIG. 1, section figure (a) showing a plan view and section figure (b) showing a lateral view of said combination.
Figure 2:

As shown in the views of FIGS. 1 and 2, the system for neuromodulation of nerves according to a first exemplary embodiment of the invention has a signal generator housing 10 which can be implanted in a human body, a wire electrode 12 extending from said signal generator housing 10 and realizing a nerve contact area 14 on one end (opposite to housing 10). As shown, in particular, in the detailed views of FIG. 2 and FIG. 3, wire electrode 12 has four poles and four shell segment electrodes (16a to 16d) which extend along an end portion of approx. 3 cm to 6 cm in the shown exemplary embodiment of the wire electrode which typically protrudes at a length between 4 cm and 31 cm from housing 12. On the end side of said nerve contact area, a fixing grommet 18 is realized at the end of the wire, wherein said fixing grommet 18 can be fixed in a suitable manner to the implantation location by means of a suture material connection by the surgeon (see representations of FIGS. 3 (a) to (d)) and allows for the fixation of the wire electrode on the end side.

On the narrow sides of signal generator housing 10, which is rectangular in the top view, mesh-like or tissue-like fixing flanges 20 realized so as to be flexible are provided and are fixed to an inner pubic bone area of the human pubic bone (PB) by means of known methods such as nailing or clamping; openings which are already shaped into the fixing flanges facilitate said fixation.

Figure 3:
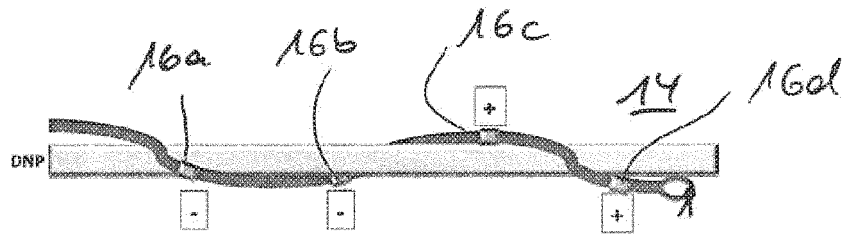
FIG. 3 shows, in section figures (a) to (d), detailed views of the nerve contact area of the wire electrode means which realize four shell segment electrodes in the present case and which have different available signal control states and corresponding polarities.
Figure 3:
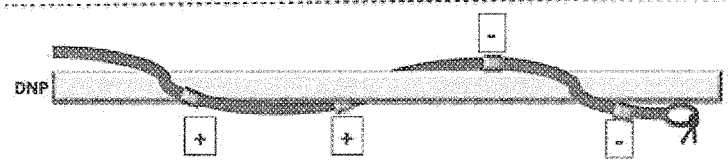
Figure 3:
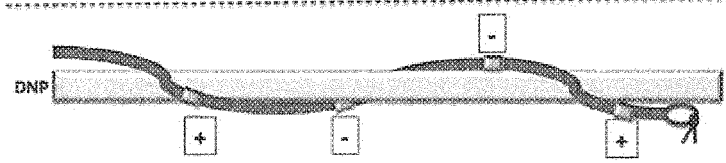
Figure 3:
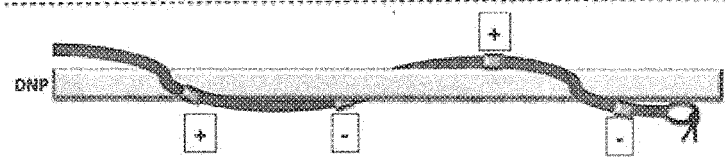

In the shown exemplary embodiment, nerve contact area 14 (or shell segment electrodes 16a to 16d provided thereon) of the wire electrode is connected to a section of the penis dorsal nerve (DNP), the electrode wire being wound around the shown section of the DNP by approx. 1.5 windings, in particular shown in the enlarged views of FIG. 3; section figures (a) to (d) of FIG. 3 illustrate possible polarities of a (DC) control signal, but said polarities are purely illustrative and can be controlled and configured in a different manner, in particular as alternating signals.

Figure 4:
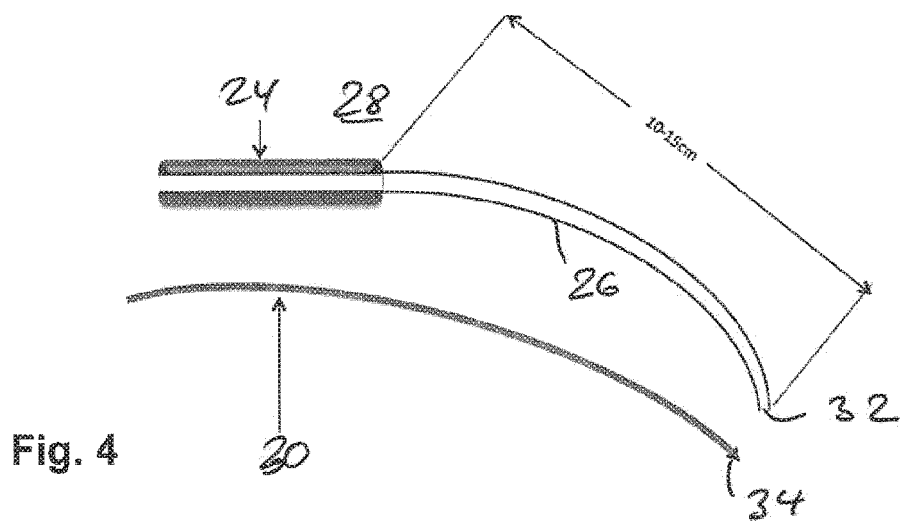
FIG. 4 is a schematic view of the electrode wire guide sleeve in an embodiment of the system of the shown exemplary embodiment according to an exemplary embodiment which has a grip or guide section and a point section which is realized for penetrating body tissue, the representation of FIG. 4 also showing a mandrel for the insertion into said sleeve in the lower area, said mandrel being removable at the target position of the guide means inside the body.
Figure 5:
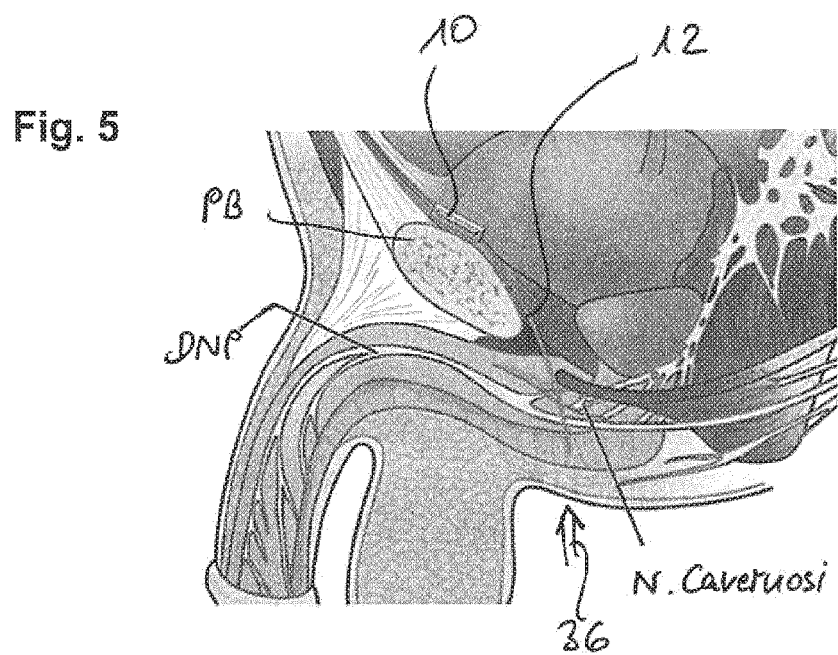
FIG. 5 is an anatomical sectional view through the genital area of the human body and a signal generator housing provided in a schematic manner on the inside of the pubic bone and wire electrode means which extend from said signal generator housing into the nerve area and which are defined according to their course through the guide means according to FIG. 4.

FIG. 4 (the result of the implantation is shown in FIG. 5) shows an additional advantageous embodiment of the invention in the form of an electrode wire guide tool which is assigned to the system: Shown sleeve 28 which has a operation section 24 and a curved section 26 can be used in a reliable manner, in particular by less experienced surgeons, in order to take the electrode wire (of the device according to FIGS. 1 to 3, for example) to a desired implantation position, as is shown in the schematic anatomical view of FIG. 5: Concretely, tool 28, which has mandrel 30 which is initially inserted into tool 28 (lower part of FIG. 4) and which realizes a point 34 which protrudes from an operation opening 32 of sleeve tool 28 on the side of the operation or on the end side, allows to guide said tool combination from the extracorporeal, i.e. along arrow directions 36 in FIG. 5, through the human tissue to pubic bone area PB. Signal generator housing 10 is usually already fixed to pubic bone area PB by surgery, for example in the manner shown in FIG. 1, or contacts said location. When point 34 (protruding from end portion 32) reaches said bone area, the surgeon removes mandrel 30 by pulling out and wire electrode 12 is then inserted through the now hollow interior of the sleeve of tool 28 along the predefined curvature of section 26 and is taken to the contact area with housing 10. The effect of the subsequent pulling out of tool 28 (against arrow direction 36) is that wire electrode 12 already contacts the nerve in the correct contact position without the risk of injuries or similar surgical errors.

Even though the system shown in an exemplary manner in the exemplary embodiment is particularly suitable for the neuromodulation of nerves for sexual stimulation, the present invention is not limited to said indication. The present invention can rather be used for any indication relating to a neuromodulation or stimulation of nerves in which a simple and safe implantability is to be combined with the best fixability and safe operating characteristics.

The invention claimed is:

1. A system for neuromodulation of nerves and configured to be implanted in a human body and having electronic signal generating means provided in an implantable signal generator housing (10),
the system comprising:
voltage supply means connected or connectable to the signal generating means,
at least one elongated multi-channel wire electrode means (12) connected or connectable to the signal generator housing and configured for implantation in the human body on a nerve (DNP), said multi-channel wire electrode means comprising a plurality of shell segment electrodes (16a-16d) on a nerve contact area (14) and, on ends thereof, being provided with fixing means (18) for anchoring the wire electrode means to an implantation location,
the signal generator housing having a flat fixing section (20) which sits and/or protrudes in the manner of a flange and/or a piece of tissue and which allows for surgical fixation of the signal generator housing to a tissue, muscle or bone area (PB) in the body, to a muscle portion and/or to a fascia, and
sleeve-like, curved electrode wire guide means (28) comprising a sleeve-shaped guide section (26) and a handle (24) attached to the sleeve-shaped guide section (26) at one end, wherein the handle (24) has an outside diameter that is greater than an outside diameter of the sleeve-shaped guide section (26); wherein the sleeve-shaped guide section can be manually operated via the handle (24), for penetrating tissue of the human body from the extracorporeal at an implantation area, and for guiding the wire electrode means (12) in the sleeve-shaped guide section (26) of the electrode wire guide means and, for inserting the wire electrode means (12) into the sleeve-shaped guide section (26) from the intracorporeal,
wherein the curved electrode wire guide means (28) further comprises a mandrel (30) which can be inserted into the sleeve-shaped guide section and which can be detached from an end portion on the body side of the electrode wire guide means, opposite to the handle, by pulling out when the curved electrode wire guide means are inserted into the body.

2. The system according to claim 1, wherein the fixing section is elastically deformable and has openings which are disposed in the form of a regular shaped pattern and/or is a nonwoven fabric, polymer material, mesh and/or tissue which can be penetrated by fixing means in the form of suture material, screws, nails or clamps.

3. The system according to claim 1, wherein the fixing section (20) axially protrudes on both ends from narrow sides of an elongated signal generator housing.

4. The system according to claim 1, wherein the fixing means of the wire electrode means are a grommet (18) which allows for a fixation by means of suture material on the free end of the wire electrode means (12).

5. The system according to claim 1, wherein the signal generator housing has a detachable plug or socket assembly for connection to the voltage generating means which are, at least partially, provided outside the housing in an implantable voltage supply housing.

6. The system according to claim 5, wherein the voltage supply housing is contactable by the plug or socket connection via a flexible voltage supply cable which is provided for implantation.

7. The system according to claim 1, wherein the voltage generating means have a battery which is chargeable.

8. The system according to claim 7, wherein the battery is chargeable in an inductive manner from the extracorporeal.

9. The system according to claim 1, wherein the voltage generating means comprise implantable voltage generating means which convert thermal energy of the body into electrical energy.

10. The system according to claim 1, wherein the signal generator housing is configured for common, detachable, connection of a plurality of multi-channel wire electrodes for defining the wire electrode means.

11. The system according to claim 1, further comprising control, parameterizing and/or operating mode means configured for wireless communication with the signal generating means in an implanted state of the signal generator housing and configured for extracorporeal operation.

12. The system according to claim 11, wherein the control, parameterizing or operating mode means are configured for user-identifying and/or device-identifying communication with the signal generating means and/or wherein the control, parameterizing or operating mode means have means for acoustic and/or optical representation, for the visualization on a display unit, of a configuration, voltage generating and/or operating mode of the signal generating means.

13. The system according to claim 11, wherein said control, parameterizing and/or operating mode means is configured for mobile or portable operation and for manual handling.

14. The system according to claim 1, wherein the wire electrode means are connected in an undetachable manner to the signal generator housing and/or wherein the signal generating means provided in the signal generator housing are configured for generating a single predefined signal generating pattern for the wire electrode means, the signal generating pattern being adapted to a number and/or orientation of shell electrode segments of the wire electrode means.

15. The system according to claim 1, comprising a plurality of the implantable signal generator housings, the signal generator housings being connected and/or connectable to one another in an electronic and signal-conducting manner and/or supply voltage manner by means of detachable wire-shaped connecting means in an implanted state in a common body.

16. The system according to claim 1, wherein the at least one elongated multi-channel wire electrode means (12) is configured for implantation in the human body in the pelvic floor and/or abdominal area, and wherein the flat fixing section (20) allows for surgical fixation to an area of the pubic bone.

17. The system according to claim 1, wherein the mandrel (30) defines a point (34) which allows for penetration.

18. The system according to claim 1, wherein a length of the sleeve-shaped guide section (26) from the handle to the end portion on the body side of the electrode wire guide means is 10-15 cm.

* * * * *